United States Patent [19]

Welply

[11] Patent Number: 5,070,021

[45] Date of Patent: Dec. 3, 1991

[54] METHOD OF MODIFYING OLIGOSACCHARIDE STRUCTURE OF TISSUE PLASMINOGEN ACTIVATOR

[75] Inventor: Joseph K. Welply, St. Peters, M

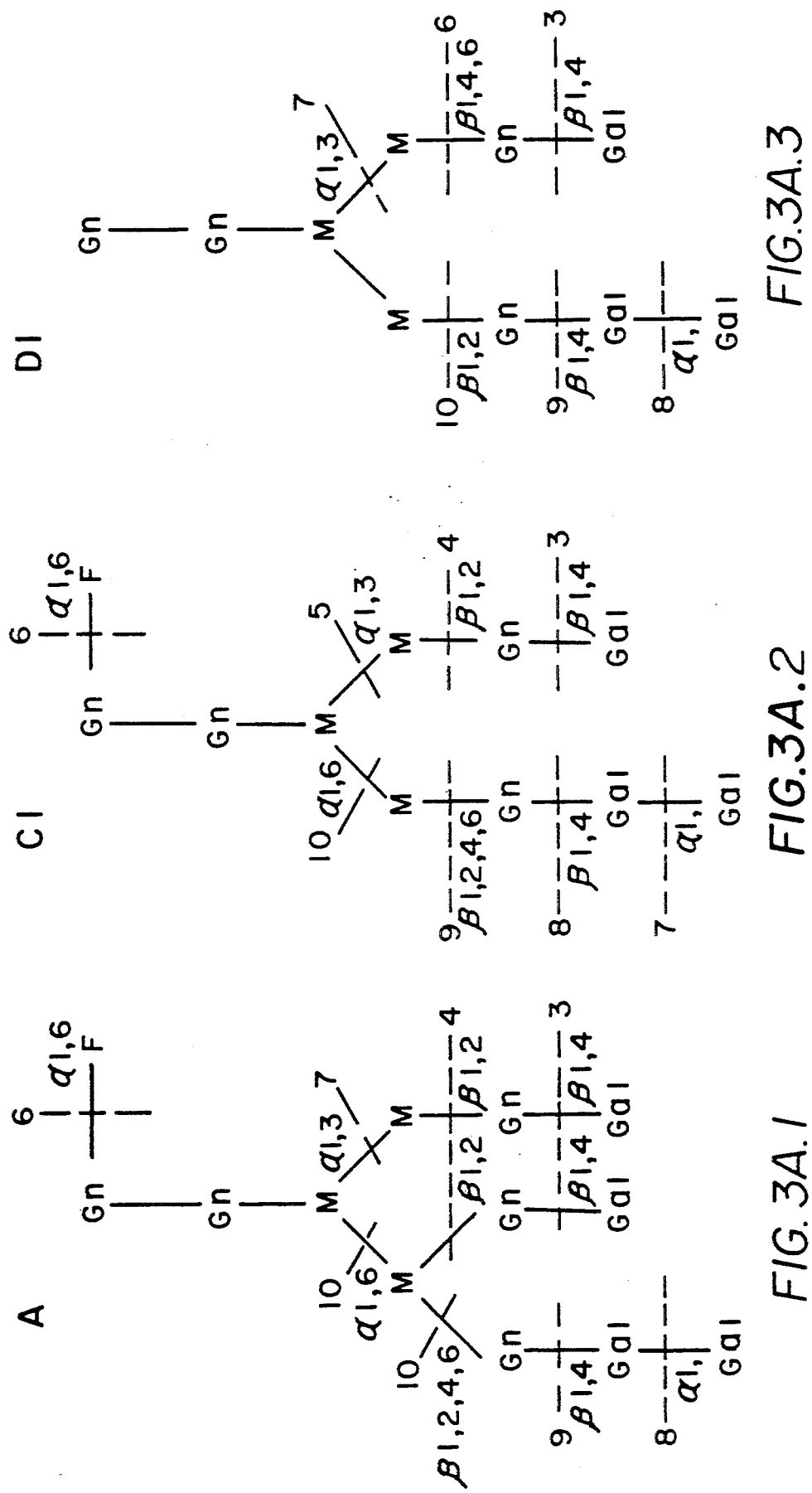
FIG.3A.1  FIG.3A.2  FIG.3A.3

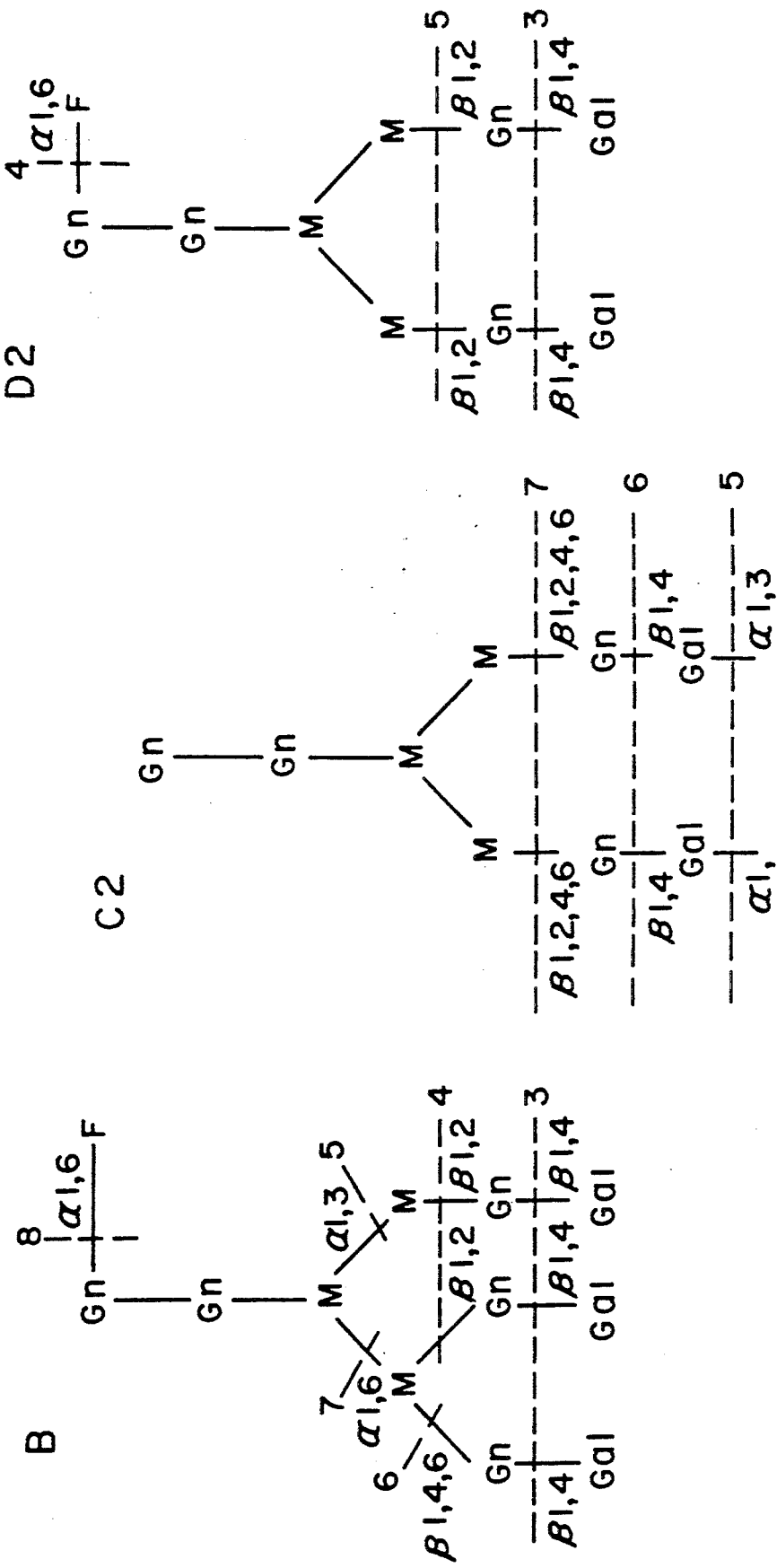
FIG.3B.3
FIG.3B.2
FIG.3B1

METHOD OF MODIFYING OLIGOSACCHARIDE STRUCTURE OF TISSUE PLASMINOGEN ACTIVATOR

BACKGROUND OF THE INVENTION

This invention relates to a method of modifying a glycoprotein's oligosaccharide structure.

Many proteins of biological and pharmaceutical interest have oligosaccharides attached to their polypeptide backbone. Although proteins produced by *E. coli* and other bacteria are non-glycosylated, proteins secreted by yeasts and mammalian cells are normally glycosylated. The sugar chains of these glycoproteins can be attached by an N-glycosidic bond to the amide group of asparagine residues (Asn-linked oligosaccharides) or by an O-glycosidic bond to the hydroxyl group of serine or threonine residues (Ser- or Thr-linked oligosaccharides).

In the Asn-linked oligosaccharides, the types of structures found on native proteins can be generally classified as high mannose, hybrid and complex type sugar chains. However, considerable variation in these basic structures is common. See, for example, the 16 oligosaccharide structures on a tissue plasminogen activator derived from normal human colon fibroblast cells as described in U.S. Pat. No. 4,751,084. Further background information on the assembly of Asn-linked oligosaccharides can be had by reference to Kornfeld and Kornfeld, *Ann. Rev. Biochem.* 54, 631–664 (1985).

The carbohydrate structure of a glycoprotein can have a significant effect upon its biological activity. That is, the oligosaccharides can affect the protein's antigenicity, stability, solubility and tertiary structure. The carbohydrate side-chains also can influence the protein's half-life and target it to receptors on the appropriate cells. The carbohydrate residues can affect both inter- and intracellular recognition. The sugar groups thus can control the relative effectiveness of a therapeutic protein when administered to a patient. These and other such functions of the carbohydrate moiety of glycoproteins are discussed, for example, by Delente, *Trends in Biotech.* 3(9), 218 (1985); van Brunt, *Bio/Technology* 4, 835–839 (1986); and Taunton-Rigby, *Biotech USA 1988*, Proc. Conf. San Francisco, Nov. 14–16, 1988, pp. 168–176.

It is also apparent that differences in the glycosylation pattern (i.e., particular structure at a specific site) on similar proteins or proteins with identical amino acid sequences can have profound effects on antigenicity, metabolism and other physiological properties. See, for example, the association of rheumatoid arthritis and osteoarthritis with changes in the glycosylation pattern of total serum by Parekh et al., *Nature* 316, 452–457 (1985) and in U.S. Pat. No. 4,659,659.

Another example of a glycoprotein in which significant biological activity resides in the oligosaccharide moieties is that of human chorionic gonadotropan (hCG). Thus, it is known that hCG without carbohydrate is a competitive inhibitor of native hCG; that oligosaccharides isolated from hCG inhibit action of native hCG; and that tumor-produced hCG having the same amino acid sequence as native hCG but different sugars has almost no biological activity. See Calvo et al., *Biochemistry* 24, 1953–1959 (1985); Chen et al., *J. Biol. Chem.* 257, 14446–14452 (1982).

Yet another group of proteins in which the presence and/or structure of the oligosaccharides can have important biological effects are the plasminogen activators (PA), namely urokinase (u-PA) and tissue plasminogen activator (t-PA). The functional properties of carbohydrate-depleted t-PA are discussed ty Little et al., *Biochemistry* 23, 6191–6195 (1984), and by Opdenakker et al., "EMBO Workshop on Plasminogen Activators," Amalfi, Italy, Oct. 14–18, 1985. The latter scientists report that enzymatic cleavage of carbohydrate sidechains from melanoma (Bowes) derived t-PA by treatment with α-mannosidase causes an increase in the biologic activity of the modified t-PA. The Bowes melanoma t-PA is a glycoprotein which has a molecular weight of about 68,000–70,000 daltons and a 527 amino acid structure with serine at the NH$_2$-terminus. The melanoma t-PA can exist as two chains, an A-chain and a B-chain. It also separates into two variants (or isoforms) in the A-chain, known as types I and II, which differ by about M$_r$ 2000–3000. See Ranby et al., *FEBS Lett.* 146 (2), 289–292 (1982), and Wallen et al., *Eur. J. Biochem.* 132, 681–686 (1983). Type I is glycosylated at Asn-117, Asn-184 and Asn-448, whereas Type II is glycosylated only at Asn-117 and Asn-448 according to Pohl et al., *Biochemistry* 23, 3701–3703 (1984). A high mannose structure has been assigned to Asn-117, whereas two complex carbohydrate structures are assigned to Asn-184 and Asn-448 by Pohl et al., "EMBO Workshop on Plasminogen Activators," Amalfi, Italy, Oct. 14–18, 1985, and *Eur. J. Biochem.* 170, 69–75 (1987).

It is known that the normal t-PA molecule has five functional domains or regions: A fibronectin-like finger domain (F); an epidermal growth factor region (GF); two kringle regions (K1 and K2); and a serine protease region (SP). The full t-PA molecule thus can be represented as F+GF+K1+K2+SP. In the 527 amino acid sequence of the normal t-PA molecule described by Pennica et al., *Nature* 301, 214–221 (1983), the finger region comprises residues 1–43; the growth factor region comprises residues 44–91; kringle refers to a characteristic triple disulfide structure of which t-PA has two such regions, K1 - residues 92–173, and K2 - residues 180–261; and the serine protease comprises residues 262–527. The SP catalytic site is formed from the His-322, Asp-371 and Ser-478 residues. Various deletions of one or more of these regions together with elimination of one or more of the glycosylation sites such as by site-directed mutagenesis have been described heretofore.

In European Patent Application 178,105, published Apr. 16, 1986, a modified t-PA is described in which one or more of the glycosylation sites have been eliminated by site-directed mutagenesis of Asn to Gln at the glycosylation sites in the kringle and serine protease regions. The amino acid residues Asn-120, -187 and -451 in the described uterine t-PA are equivalent to residues Asn-117, -184 and -448, respectively, in the Bowes melanoma t-PA.

A variety of site-mutagens are also described in European Patent Application 227,462, published July 1, 1987, including mutagenesis at the above glycosylation sites and at the cleavage sites in the region 272–280, especially in the sequence Phe(274)-Arg(275)-Ile(276)-Lys(277).

According to European Patent Application 238,304, published Sept. 23, 1987, melanoma t-PA devoid of carbohydrate structure at amino acid residue 117 but unmodified from native t-PA in functional carbohydrate structure at amino acid residues 184 and/or 448 retains substantially full biological activity compared to native t-PA but has increased in vivo half-life. See also Hotchkiss et al., Thromb. Haemostasis 60, 255-261 (1988).

In U.S. Pat. No. 4,751,084, a glycosylated t-PA obtained from cultured normal human colon fibroblast cells was found to have a unique, heterogeneous glycosylation pattern that differs significantly from the t-PA of Bowes melanoma although the protein moieties are substantially similar. Differences in biological activities such as thermal stability and fibrin stimulatory properties were shown to be caused by the specific glycoforms present.

The role of specific sugar units on the clearance of t-PA from circulation is further discussed, for example, by Lucore et al., *Circulation* 77 (4), 906-914 (1988).

It is thus apparent that methods of modifying a glycoprotein's oligosaccharide structure can have substantial importance to protein research for the development of biopharmaceuticals through carbohydrate engineering.

BRIEF DESCRIPTION OF THE INVENTION

In accordance with the present invention a method for modifying a glycoprotein's oligosaccharide structure is provided which comprises substituting or deleting an amino acid residue at a position which is non-adjacent or remote from the glycosylation site.

In a preferred embodiment of the invention, an amino acid substitution is made at a cysteine residue to disrupt a disulfide bridge remote from the glycosylation site.

The method of the invention is especially adapted to modification of the oligosaccharide structure of plasminogen activators, namely urokinase u-PA) and tissue plasminogen activator (t-PA). In particular, disruption of a disulfide bridge in the growth factor domain can have a profound effect upon the oligosaccharide structure at a remote glycosylation site in a kringle region. For example, disruption of a disulfide bridge in the growth factor domain of t-PA can cause modification of the oligosaccharide structure at the glycosylation site in the kringle 1 (KI) region, namely Asn-117, as well as at other glycosylation sites such as Asn-184 and Asn-448. Thus, in an illustrative example of the present invention, substituting an arginine residue for cysteine at amino acid position 73 in a recombinant t-PA produced in C-127 mouse cells results in a modified oligosaccharide structure at Asn-117. The oligosaccharide is changed from that of a high mannose type to a complex type oligosaccharide. This modified t-PA can be represented as t-PA[Cys(73)→Arg; Asn-117, complex oligosaccharide glycoform]or, alternatively, as F+GF[Cys(73-)→Arg]+K1+K2+SP. Similar such disruptions of a disulfide bridge can be made by substituting an arginine residue for cysteine at any of amino acid positions 51, 56, 62, 75 and 84 in the growth factor domain of t-PA, with substantially similar effects upon the oligosaccharide structure at Asn-117. As used herein, the numbering of the 527 amino acid sequence of the normal t-PA molecule is that described by Pennica et al., *Nature* 301, 214-221 (1983).

In a like manner, disruption of a disulfide bridge in the growth factor region of urokinase can produce modification of the oligosaccharide structure at a remote glycosylation site of the molecule. For example, substituting an arginine residue for cysteine at amino acid position 42 can have an effect on the oligosaccharide structure at Asn-302. As used herein, the numbering of the 411 amino acid sequence of the normal urokinase molecule is that described by Holmes et al., *Bio/Technology* 3, 923-929 (1985).

DETAILED DESCRIPTION OF THE INVENTION

Figure 1A:
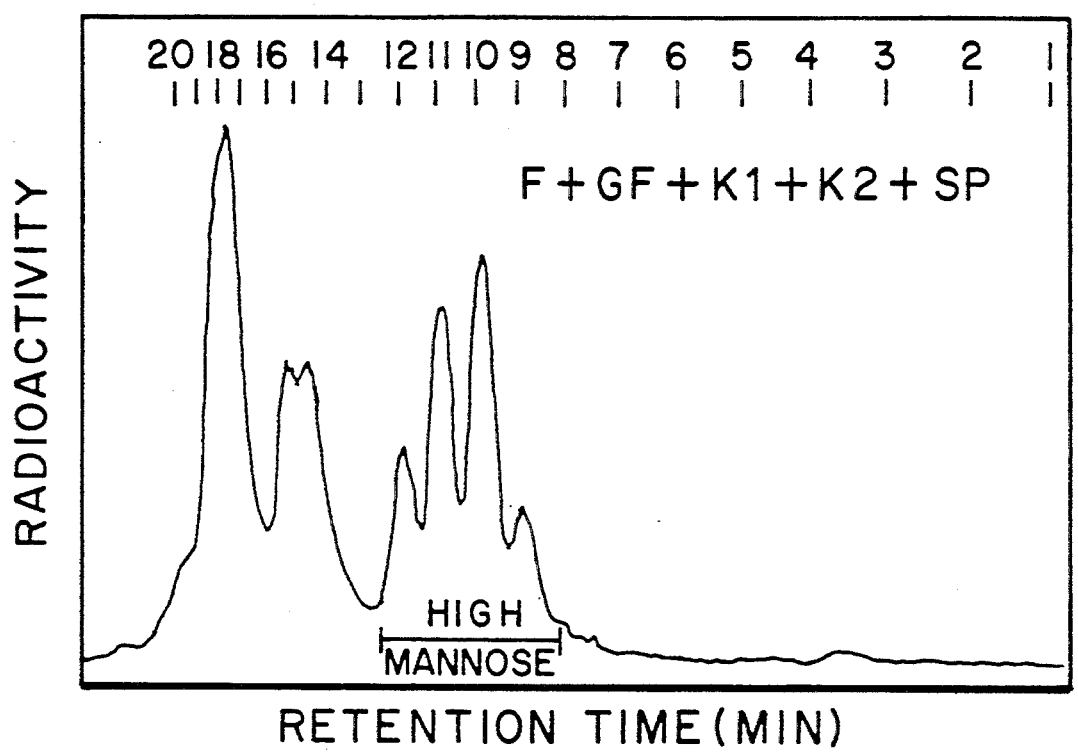
Figure 1B:
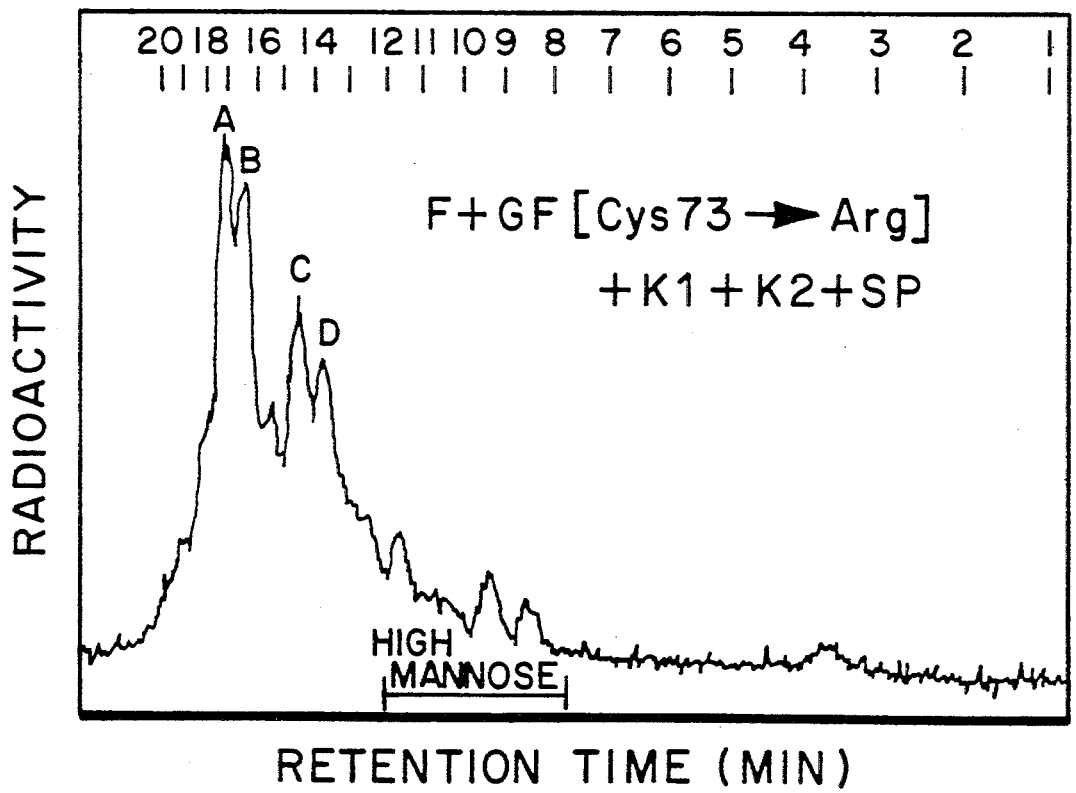

While the specification concludes with claims particularly pointing out and distinctly claiming the subject matter regarded as forming the present invention, it is believed that the invention will be better understood from the following detailed description of preferred embodiments of the invention taken in conjunction with the appended drawings in which:

FIG. 1 is a graphical representation which shows the Bio-Gel P-4 column chromatography profile of the oligosaccharides released by hydrazinolysis from (A) native t-PA (upper panel) and (B) modified t-PA F+GF[Cys(73)→Arg]+K1+K2+SP after neuraminidase digestion. The numbers at the top indicate glucose units (g.u.). High mannose fractions are indicated with a bar whereas the complex oligosaccharide fractions are designated A, B, C and D. Radioactivity is shown on the vertical scale and retention time in minutes on the horizontal scale.

Figure 2:
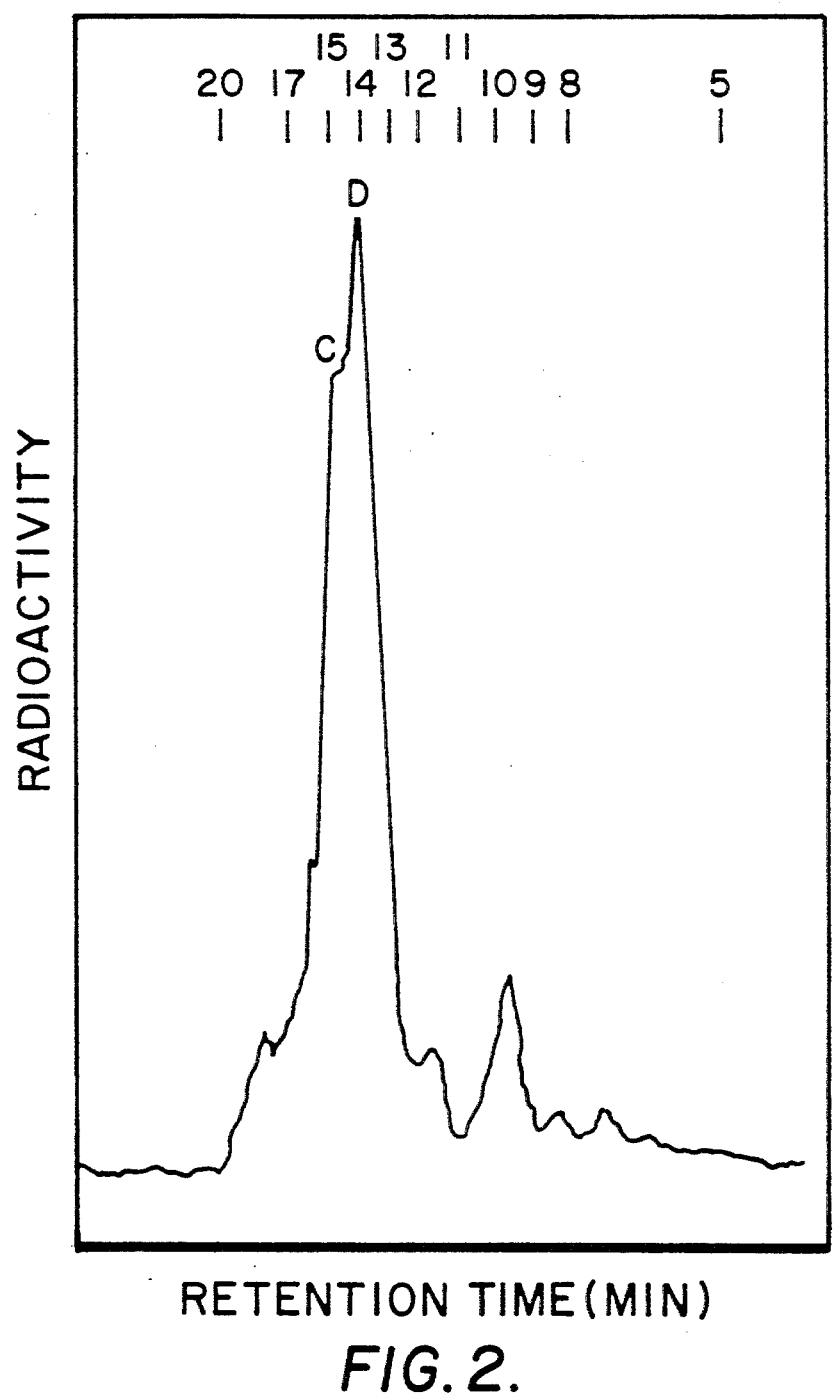

FIG. 2 is a graphical representation which shows the Bio-Gel P-4 column chromatography profile of the oligosaccharides isolated as in FIG. 1 from a tryptic peptide containing the glycosylation site Asn-117 of modified t-PA F+GF[Cys(73)→Arg]+K1+K2+SP The complex oligosaccharide fractions are designated C and D and correspond to fractions C and D in panel (B) of FIG. 1.

FIG. 3 (A) and (B) show the structures of the six major oligosaccharides liberated from t-PA MB1023.

The invention is illustrated in one embodiment by the modified t-PA disclosed in copending U.S. patent application Ser. No. 149,793, filed Jan. 29, 1988, now U.S. Pat. No. 4,963,357, and assigned to a common assignee. The modified t-PA was prepared from a chemically synthesized gene coding for t-PA with a single point mutation of Arg for Cys at residue 73. In this embodiment, also designated herein as t-PA variant MB1023, the mature protein has a 527 amino acid structure in which residue 73 is arginine instead of the cysteine that is present in native t-PA. This variant was prepared by using an oligonucleotide sequence in the construction of the synthetic gene which codes for Arg instead of Cys at the appropriate position.

The gene coding for this illustrative modified t-PA can be cloned into and expressed in prokaryotic and eukaryotic hosts. For example, active modified t-PA protein can be expressed in a prokaryotic host such as *E. coli* or a eukaryotic host such as Chinese hamster ovary (CHO) cells or C-127 mouse cells by operably inserting the modified t-PA coding sequence in replicable expression vectors or plasmids. For example, it can be inserted into a suitable plasmid such as pML for production in *E. coli* and the bovine papilloma virus (BPV) vector for production in mouse cells or a shuttle vector which can replicate in both prokaryotic and eukaryotic cells. In a preferred embodiment as used herein, the gene coding for the t-PA sequence t-PA[-Cys(73)→Arg] was cloned into and expressed from C-127 mouse cells. The excreted protein was extracted from the cell media by concentration and then purified on an affinity chromatography column.

A preferred cloning vector containing the nucleotide sequence for the t-PA variant MB1023 is plasmid pMON1401. This plasmid carried in a mouse C-127 host cell is on deposit with the American Type Culture Collection, Rockville, Md., under accession number ATCC CRL 9614. Other suitable eukaroytic and prokaryotic hosts for expression of the illustrative modified t-PA used in this invention will be readily apparent to the person skilled in the art after reading the present disclosure.

Determination of the structure of the oligosaccharides from the glycoprotein employs adaptation of the method used for Immunoglobulin G-derived asparagine-linked oligosaccharides as described by Rademacher and Dwek, *Prog. Immunol.* 5, 95–112 (1983) and Parekh et al., *Nature* 316, 452–457 (1985). According to this method, the glycoprotein sample is subjected to controlled hydrazinolysis to release intact its associated oligosaccharide moieties as described by Takahasi et al., *Meth. Enzymol.* 83, 263–268 (1982). Reduction of the reducing terminal N-acetylglucosamine residues using $NaB^3H_4$ is then performed to label radioactively each carbohydrate chain. Each labeled oligosaccharide mixture is then subjected to exhaustive neuraminidase digestion in order to analyze the distribution of neutral structures. The resulting 'asialo' oligosaccharide mixtures are then fractionated by Bio-Gel® P-4 (~400 mesh) gel filtration chromatography, which separates neutral oligosaccharides on the basis of the effective hydrodynamic volumes as described by Yamashita et al., *Meth. Enzymol.* 83 105–126 (1982). Bio-Gel P-4 is a gel filtration material of choice for analysis of reduced oligosaccharides by gel permeation chromatography due to the polyacrylamide structure. Bio-Gel P is prepared by copolymerization of acrylamide with N,N'-methylene bis-acrylamide. P-4 has an exclusion limit and fractionation range of about 800–4000 daltons. This well-known gel filtration material is commercially available from Bio-Rad Laboratories, Richmond, Calif.

The oligosaccharides also can be initially isolated from the glycoprotein by the method described in U.S. Pat. Nos. 4,719,294 and 4,736,022. Said method employs hydrazinolysis of the glycoprotein under reaction conditions to cause cleavage at the N-linked sites, producing a mixture having as a major component a de-N-acetylated hydrazone derivative of the oligosaccharides, followed by N-acylation of the hydrazone derivative, acid-catalysis of the hydrazone derivative to produce unreduced oligosaccharides and subjecting the resulting unreduced oligosaccharides to cellulose column chromatography to remove contaminants and to recover the unreduced oligosaccharides. The latter materials, being essentially pure, can be used for attachment to various peptide or protein chains for further study.

Adaptation of these oligosaccharide structure determination methods to t-PA is disclosed in U.S. Pat. No. 4,751,084, the disclosure of which is incorporated herein by reference.

In an illustrative example of this invention, the modified t-PA MB1023 and, as a control, native t-PA were subjected to hydrazinolysis, radiolabeled with sodium borotritide, treated with neuraminidase to remove sialic acid residues and co-chromatographed with unlabeled dextran polymers on Bio-Gel P-4. The P-4 patterns for the oligosaccharides of MB1023 are shown in FIG. 1. As can be seen, the MB1023 profile contains only a small amount of radioactive oligosaccharide at glucose positions ranging from 9–12, corresponding to high mannose chains, whereas the native t-PA expressed in C-127 mouse cells contains a substantial amount of high mannose oligosaccharides.

Determination of the structures of the six major oligosaccharides liberated from t-PA MB1023 (shown in FIG. 3) was made by conventional methods of sequential exoglycosidase digestion as described in U.S. Pat. No. 4,751,084, Ex. 2. See also Kobata in "Biology of Carbohydrates," Ginsburg and Robbins, Eds., John Wiley and Sons, pp. 87–162 (1984); Snider, Ibid., pp. 163–193. The following symbols are used to indicate monosaccharide or other structural units and their residues in the oligosaccharides:

Galactose - Gal
Mannose - M
Fucose - F
N-Acetylglucosamine - Gn

The dash lines between monosaccharide units represent enzyme cleavage points. The six oligosaccharides shown belong to the bi- and triantennary classes.

Tryptic peptides containing the glycosylation sites of the modified t-PA MB1023 were obtained by digestion of the glycoprotein with trypsin and fractionating the resulting mixture by reverse phase HPLC by conventional methods similar to those described, for example, by Pohl et al., Biochem. 23, 3701–3707 (1984); Vehar, Bio/Technology 2, 1051–1057 (1984); and U.S. Pat. No. 4,751,084, Ex. 3. The tryptic glycopeptide fraction containing glycosylation site Asn-117 was subjected to procedure for isolation of the oligosaccharide fractions, as above, and the Bio-Gel P-4 pattern is shown in FIG. 2. As can be seen, the Asn-117 site of MB1023 contains only a small amount of radioactive oligosaccharide at those glucose positions corresponding to high mannose chains; whereas, it is known that the Asn-117 note in native t-PA contains significant high mannose.

It will be appreciated that other mutations can be made to shift a glycosylation site of the glycoprotein from its normal position to another potential glycosylation site and then a disulfide bridge can be disrupted to modify the oligosaccharide structure as described hereinbefore. For example, the glycosylation site in kringle 1 of t-PA can be shifted from position 117 to 104 by mutating Asn-117→Ser and Trp-104→Asn, or shifted from position 117 to 125 by mutating Asn-117→Ser and Pro-125→Asn, and then a disulfide bridge can be disrupted by mutating Cys-73→Arg.

Various other examples will be apparent to the person skilled in the art after reading the present disclosure without departing from the spirit and scope of the invention. It is intended that all such other examples be included within the scope of the appended claims.

What is claimed is:

1. The method of modifying the oligosaccharide structure of human t-PA which comprises substituting Arg for Cys at any of amino acid residues 51, 56, 62, 73, 75 or 84 in said t-PA to thereby modify the oligosaccharide structure at Asn-117 from a high mannose type to a complex type oligosaccharide structure and expressing said t-PA in C-127 cells.

2. The method of claim 1 in which the substitution is made at amino acid residue 73.

* * * * *